(12) United States Patent
DeVore et al.

(10) Patent No.: US 7,476,203 B2
(45) Date of Patent: Jan. 13, 2009

(54) DEVICE AND METHOD FOR MEASURING THE DIAMETER OF AN AIR PASSAGEWAY

(75) Inventors: Lauri J. DeVore, Seattle, WA (US); William A. Sirokman, Kirkland, WA (US); James M. Kutsko, Woodinville, WA (US); David H. Dillard, Redmond, WA (US); Peter R. Westman, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 0 days.

(21) Appl. No.: 11/260,012

(22) Filed: Oct. 26, 2005

(65) Prior Publication Data
US 2006/0155217 A1    Jul. 13, 2006

Related U.S. Application Data

(63) Continuation of application No. 10/254,392, filed on Sep. 24, 2002, now abandoned.

(51) Int. Cl.
*A61B 5/117* (2006.01)
*A61B 5/103* (2006.01)

(52) U.S. Cl. ...................................... 600/587
(58) Field of Classification Search ................ 600/587, 600/593, 505, 549, 114, 103, 119, 120, 158; 604/98.01, 103.1, 104, 913, 99.03, 247, 248, 604/920; 606/41, 192, 2, 7, 15; 607/101; 128/200.26, 207.14; 137/614.2
See application file for complete search history.

(56) References Cited

U.S. PATENT DOCUMENTS 2,981,254 A    4/1961  Vanderbilt 3,657,744 A    4/1972  Ersek
3,788,327 A    1/1974  Donowitz et al.

(Continued)

FOREIGN PATENT DOCUMENTS

EP    1 151 729    11/2001

(Continued)

OTHER PUBLICATIONS

Dillard et al., "Evaluation of a Novel Intra-bronchial Valve Device to Produce Lung Volume Reduction." Poster shown at conference in Jun. 2002.

(Continued)

*Primary Examiner*—Max Hindenburg
*Assistant Examiner*—Brian Szmal
(74) *Attorney, Agent, or Firm*—Knobbe, Martens, Olson & Bear LLP

(57) ABSTRACT

The invention provides a device for measuring an inside diameter of a body lumen, such as an air passageway. The device includes a flexible catheter having an inflation lumen, a fluid dispenser in fluid communication with the inflation lumen and operable to communicate a measurable fluid volume change with the inflation lumen, and an expandable member in fluid communication with the inflation lumen and having a known relationship between volume and a changeable transverse dimension, the transverse dimension being changeable in response to fluid volume changes of the fluid dispenser and arranged for placement adjacent to opposing portions of an interior wall of the air passageway. The expandable member may be dimensioned for transoral placement into the air passageway, and may comprise a balloon that includes a complaint material.

33 Claims, 6 Drawing Sheets

U.S. PATENT DOCUMENTS

| | | | |
|---|---|---|---|
| 4,014,318 A | 3/1977 | Dockum et al. | |
| 4,086,665 A | 5/1978 | Poirier | |
| 4,212,463 A | 7/1980 | Repinski et al. | |
| 4,250,873 A | 2/1981 | Bonnet | |
| 4,302,854 A | 12/1981 | Runge | |
| 4,610,256 A | 9/1986 | Wallace | |
| 4,654,027 A * | 3/1987 | Dragan et al. | 604/99.03 |
| 4,684,363 A * | 8/1987 | Ari et al. | 604/98.01 |
| 4,710,192 A | 12/1987 | Liotta et al. | |
| 4,732,152 A | 3/1988 | Wallsten et al. | |
| 4,759,758 A | 7/1988 | Gabbay | |
| 4,795,449 A | 1/1989 | Schneider et al. | |
| 4,808,183 A | 2/1989 | Panje | |
| 4,819,664 A | 4/1989 | Nazari | |
| 4,830,003 A | 5/1989 | Wolff et al. | |
| 4,832,680 A | 5/1989 | Haber et al. | |
| 4,846,836 A | 7/1989 | Reich | |
| 4,850,999 A | 7/1989 | Planck | |
| 4,852,568 A | 8/1989 | Kensey | |
| 4,877,025 A | 10/1989 | Hanson | |
| 4,934,999 A | 6/1990 | Bader | |
| 4,968,294 A | 11/1990 | Salama | |
| 5,061,274 A | 10/1991 | Kensey | |
| 5,116,360 A | 5/1992 | Pinchuk et al. | |
| 5,116,564 A | 5/1992 | Jansen et al. | |
| 5,123,919 A | 6/1992 | Sauter et al. | |
| 5,135,488 A | 8/1992 | Foote et al. | |
| 5,151,105 A | 9/1992 | Kwan-Gett | |
| 5,161,524 A | 11/1992 | Evans | |
| 5,171,299 A | 12/1992 | Heitzmann et al. | |
| 5,275,169 A | 1/1994 | Afromowitz et al. | |
| 5,306,234 A | 4/1994 | Johnson | |
| 5,339,805 A * | 8/1994 | Parker | 128/200.26 |
| 5,342,298 A | 8/1994 | Michaels et al. | |
| 5,352,240 A | 10/1994 | Ross | |
| 5,358,518 A | 10/1994 | Camilli | |
| 5,366,478 A | 11/1994 | Brinkerhoff et al. | |
| 5,382,261 A | 1/1995 | Palmaz | |
| 5,392,775 A | 2/1995 | Adkins, Jr. et al. | |
| 5,409,019 A | 4/1995 | Wilk | |
| 5,411,507 A | 5/1995 | Heckele | |
| 5,411,552 A | 5/1995 | Andersen et al. | |
| 5,413,599 A | 5/1995 | Imachi et al. | |
| 5,417,226 A | 5/1995 | Juma | |
| 5,445,626 A | 8/1995 | Gigante | |
| 5,486,154 A | 1/1996 | Kelleher | |
| 5,499,995 A | 3/1996 | Teirstein | |
| 5,500,014 A | 3/1996 | Quijano et al. | |
| 5,549,628 A | 8/1996 | Cooper et al. | |
| 5,562,608 A | 10/1996 | Sekins et al. | |
| 5,645,565 A | 7/1997 | Rudd et al. | |
| 5,660,175 A | 8/1997 | Dayal | |
| 5,662,713 A | 9/1997 | Andersen et al. | |
| 5,683,451 A | 11/1997 | Lenker et al. | |
| 5,693,089 A | 12/1997 | Inoue | |
| 5,697,968 A | 12/1997 | Rogers et al. | |
| 5,702,409 A | 12/1997 | Rayburn et al. | |
| 5,725,519 A | 3/1998 | Penner et al. | |
| 5,752,522 A * | 5/1998 | Murphy | 600/587 |
| 5,752,965 A | 5/1998 | Francis et al. | |
| 5,800,339 A | 9/1998 | Salama | |
| 5,840,081 A | 11/1998 | Andersen et al. | |
| 5,855,587 A | 1/1999 | Hyon et al. | |
| 5,855,597 A | 1/1999 | Jayaraman | |
| 5,944,738 A | 8/1999 | Amplatz et al. | |
| 5,947,997 A | 9/1999 | Pavcnik et al. | |
| 5,957,949 A | 9/1999 | Leonhardt et al. | |
| 5,972,009 A | 10/1999 | Fortier et al. | |
| 5,976,158 A | 11/1999 | Adams et al. | |
| 5,976,174 A | 11/1999 | Ruiz | |
| 5,984,965 A | 11/1999 | Knapp et al. | |
| 6,003,517 A | 12/1999 | Sheffield et al. | |
| 6,007,575 A | 12/1999 | Samuels | |
| 6,009,614 A | 1/2000 | Morales | |
| 6,010,511 A | 1/2000 | Murphy | |
| 6,020,380 A | 2/2000 | Killian | |
| 6,027,525 A | 2/2000 | Suh et al. | |
| 6,045,560 A | 4/2000 | McKean et al. | |
| 6,051,022 A | 4/2000 | Cai et al. | |
| 6,068,635 A | 5/2000 | Gianotti | |
| 6,068,638 A | 5/2000 | Makower | |
| 6,077,291 A | 6/2000 | Das | |
| 6,083,255 A | 7/2000 | Laufer et al. | |
| 6,096,027 A | 8/2000 | Layne | |
| 6,099,551 A | 8/2000 | Gabbay | |
| 6,124,663 A | 9/2000 | Rebuffat | |
| 6,135,729 A | 10/2000 | Aber | |
| 6,135,991 A | 10/2000 | Muni et al. | |
| 6,141,855 A | 11/2000 | Morales | |
| 6,146,357 A | 11/2000 | Addis | |
| 6,162,245 A | 12/2000 | Jayaraman | |
| 6,168,614 B1 | 1/2001 | Andersen et al. | |
| 6,174,307 B1 * | 1/2001 | Daniel et al. | 606/15 |
| 6,183,520 B1 | 2/2001 | Pintauro et al. | |
| 6,200,333 B1 | 3/2001 | Laufer | |
| 6,206,918 B1 | 3/2001 | Campbell et al. | |
| 6,234,996 B1 | 5/2001 | Bagaoisan et al. | |
| 6,240,615 B1 | 6/2001 | Kimes et al. | |
| 6,241,678 B1 | 6/2001 | Afremov et al. | |
| 6,245,102 B1 | 6/2001 | Jayaraman | |
| 6,258,100 B1 | 7/2001 | Alferness et al. | |
| 6,270,527 B1 | 8/2001 | Campbell et al. | |
| 6,293,951 B1 | 9/2001 | Alferness et al. | |
| 6,302,893 B1 | 10/2001 | Limon et al. | |
| 6,312,407 B1 | 11/2001 | Zadno-Azizi et al. | |
| 6,325,777 B1 | 12/2001 | Zadno-Azizi et al. | |
| 6,325,778 B1 | 12/2001 | Zadno-Azizi et al. | |
| 6,327,772 B1 | 12/2001 | Zadno-Azizi et al. | |
| 6,328,689 B1 | 12/2001 | Gonzalez et al. | |
| 6,355,014 B1 | 3/2002 | Zadno-Azizi et al. | |
| 6,402,754 B1 | 6/2002 | Gonzalez | |
| 6,416,554 B1 | 7/2002 | Alferness et al. | |
| 6,428,561 B1 | 8/2002 | Johansson-Ruden et al. | |
| 6,458,076 B1 | 10/2002 | Pruitt | |
| 6,485,407 B2 | 11/2002 | Alferness et al. | |
| 6,491,706 B1 | 12/2002 | Alferness et al. | |
| 6,493,589 B1 | 12/2002 | Medhkour et al. | |
| 6,510,846 B1 | 1/2003 | O'Rourke | |
| 6,514,290 B1 | 2/2003 | Loomas | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,629,951 B2 | 10/2003 | Laufer et al. | |
| 6,634,363 B1 | 10/2003 | Danek et al. | |
| 6,638,285 B2 | 10/2003 | Gabbay | |
| 6,679,264 B1 | 1/2004 | Deem et al. | |
| 2001/0025132 A1 | 9/2001 | Alferness et al. | |
| 2001/0034518 A1 * | 10/2001 | Edwards et al. | 606/41 |
| 2001/0037808 A1 | 11/2001 | Deem et al. | |
| 2001/0041906 A1 | 11/2001 | Gonzalez | |
| 2001/0052344 A1 | 12/2001 | Doshi | |
| 2002/0007831 A1 | 1/2002 | Davenport et al. | |
| 2002/0077564 A1 * | 6/2002 | Campbell et al. | 600/549 |
| 2002/0077696 A1 | 6/2002 | Zadno-Azizi et al. | |
| 2002/0087153 A1 | 7/2002 | Roschak et al. | |
| 2002/0095209 A1 | 7/2002 | Zadno-Azizi et al. | |
| 2002/0111619 A1 | 8/2002 | Keast et al. | |
| 2002/0111620 A1 | 8/2002 | Cooper et al. | |
| 2002/0112729 A1 | 8/2002 | DeVore et al. | |
| 2002/0138135 A1 | 9/2002 | Duerig et al. | |
| 2003/0018327 A1 | 1/2003 | Truckai et al. | |
| 2003/0018344 A1 | 1/2003 | Kaji et al. | |
| 2003/0050648 A1 | 3/2003 | Alferness et al. | |
| 2003/0051733 A1 | 3/2003 | Kotmel et al. | |

| | | | | | | |
|---|---|---|---|---|---|---|
| 2003/0055331 | A1 | 3/2003 | Kotmel et al. | WO | 01/54685 | 8/2001 |
| 2003/0083671 | A1 | 5/2003 | Rimbaugh et al. | WO | 01/66190 | 9/2001 |
| 2003/0127090 | A1 | 7/2003 | Gifford et al. | WO | 01/74271 | 10/2001 |
| 2003/0154988 | A1 | 8/2003 | DeVore et al. | WO | 01/89366 | 11/2001 |
| 2003/0158515 | A1 | 8/2003 | Gonzalez et al. | WO | 01/95786 | 12/2001 |
| 2003/0228344 | A1 | 12/2003 | Fields et al. | WO | 02/05884 | 1/2002 |
| 2004/0039250 | A1 | 2/2004 | Tholfsen et al. | WO | 02/32333 | 4/2002 |

FOREIGN PATENT DOCUMENTS

| | | |
|---|---|---|
| RU | 2140211 | 10/1999 |
| SU | 852321 | 7/1981 |
| WO | 94/26175 | 11/1994 |
| WO | 95/32018 | 11/1995 |
| WO | 96/34582 | 11/1996 |
| WO | 97/44085 | 11/1997 |
| WO | 98/00840 | 1/1998 |
| WO | 98/19633 | 5/1998 |
| WO | 98/39047 | 9/1998 |
| WO | 98/44854 | 10/1998 |
| WO | 99/01076 | 1/1999 |
| WO | 99/13801 | 3/1999 |
| WO | 99/26692 | 6/1999 |
| WO | 99/32040 | 7/1999 |
| WO | 99/42059 | 8/1999 |
| WO | 99/42161 | 8/1999 |
| WO | 99/64109 | 12/1999 |
| WO | 00/42950 | 7/2000 |
| WO | 00/51510 | 9/2000 |
| WO | 00/62699 | 10/2000 |
| WO | 00/78386 | 12/2000 |
| WO | 00/78407 | 12/2000 |
| WO | 01/03642 | 1/2001 |
| WO | 01/05334 | 1/2001 |
| WO | 01/10313 | 2/2001 |
| WO | 01/10314 | 2/2001 |
| WO | 01/12104 | 2/2001 |
| WO | 01/13839 | 3/2001 |
| WO | 01/28433 | 4/2001 |
| WO | 01/37897 | 5/2001 |
| WO | 01/45590 | 6/2001 |
| WO | 01/49213 | 7/2001 |
| WO | 01/54585 | 8/2001 |
| WO | 01/54625 | 8/2001 |
| WO | 02/34322 | 5/2002 |
| WO | 02/47575 | 6/2002 |
| WO | 02/056794 | 7/2002 |
| WO | 02/064045 | 8/2002 |
| WO | 02/064190 | 8/2002 |
| WO | 02/094087 | 11/2002 |
| WO | 03/022124 | 3/2003 |
| WO | 03/034927 | 5/2003 |
| WO | 03/078579 | 9/2003 |
| WO | 03/088820 | 10/2003 |
| WO | 03/099164 | 12/2003 |
| WO | 2004/010845 | 5/2004 |

OTHER PUBLICATIONS

Watanabe et al.: Bronchial Embolization Using Dental Impression Material in a Case of Pyelo-broncial Fistula with Candida Fungemia; 1991. Journal of the Japan Society for Bronchology, pp. 607-610.

Harris et al., "The Experimental Production in Dogs of Emphysema with Associated Asthmatic Syndrome by Means of an Intrattracheal Ball Valve," J. Exp Med 30:1919; 75-88.

Lewis et al., "Pulmonary Interstitial Emphysema: Selective Bronchial Occlusion with a Swan-Ganz Catheter." Archives of Disease in Childhood, 63:1988, 313-315.

Mathew et al. "Selective Bronchial Obstruction for Treatment of Bullous Interstitial Emphysema," J. of Ped. 96:1980, 475-477.

Puhakka et al., "Acute Bronchial Obstruction: An Experimental Rabbit Model Study." Int. J. of Pediatric Otorhinolaryngology. 18:1989, 107-118.

Snider et al., "The Definition of Emphysema: Report of the National Heart Lung and Blood Institute, Division of Lung Diseases Workshop", Am. Rev. Respir. Dis., 132:182-185, 1985.

Article: Autocath®100—Nonsurgical, Intraurethral Bladder Control Device for Incontinent and Retentive Women—Dr. Kulisz's Development.

* cited by examiner

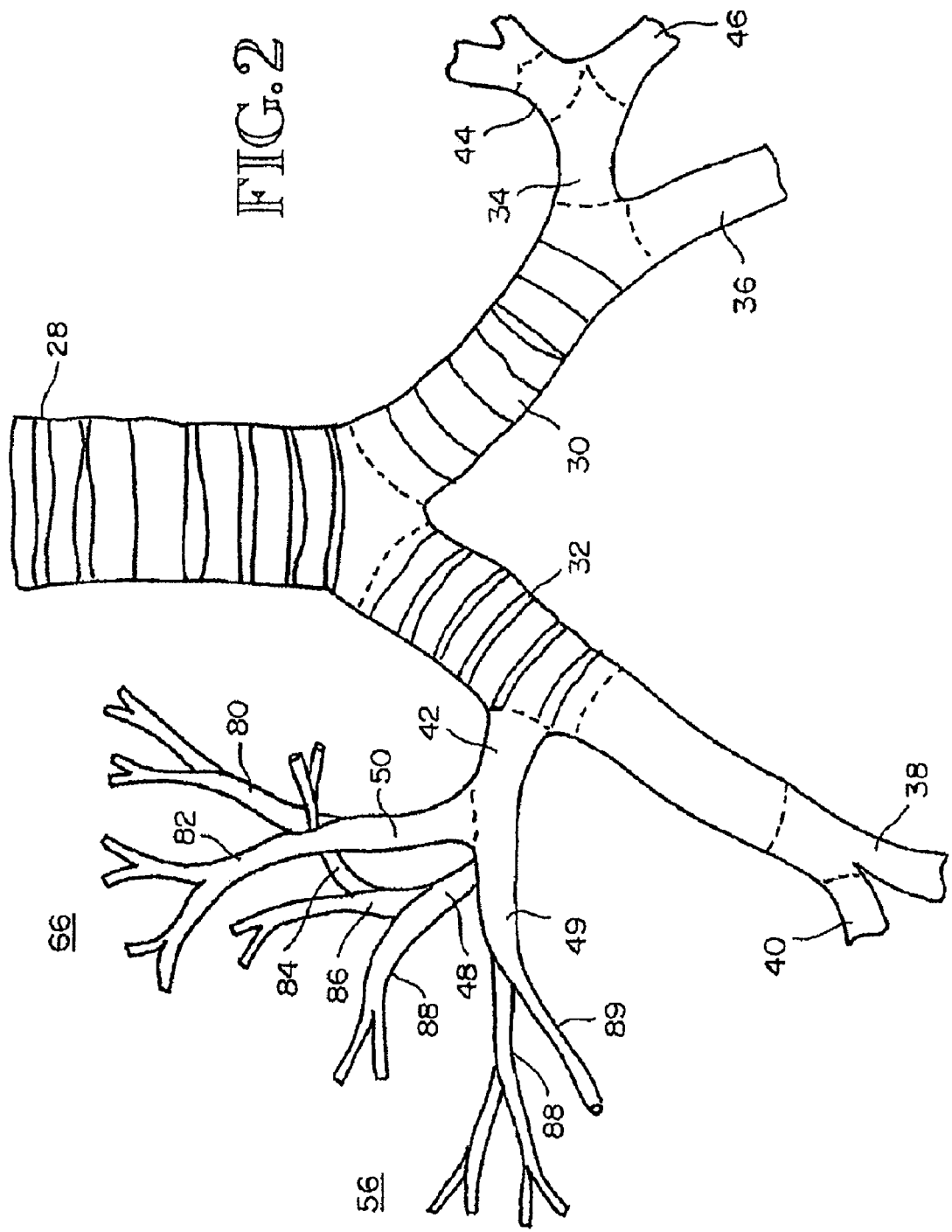

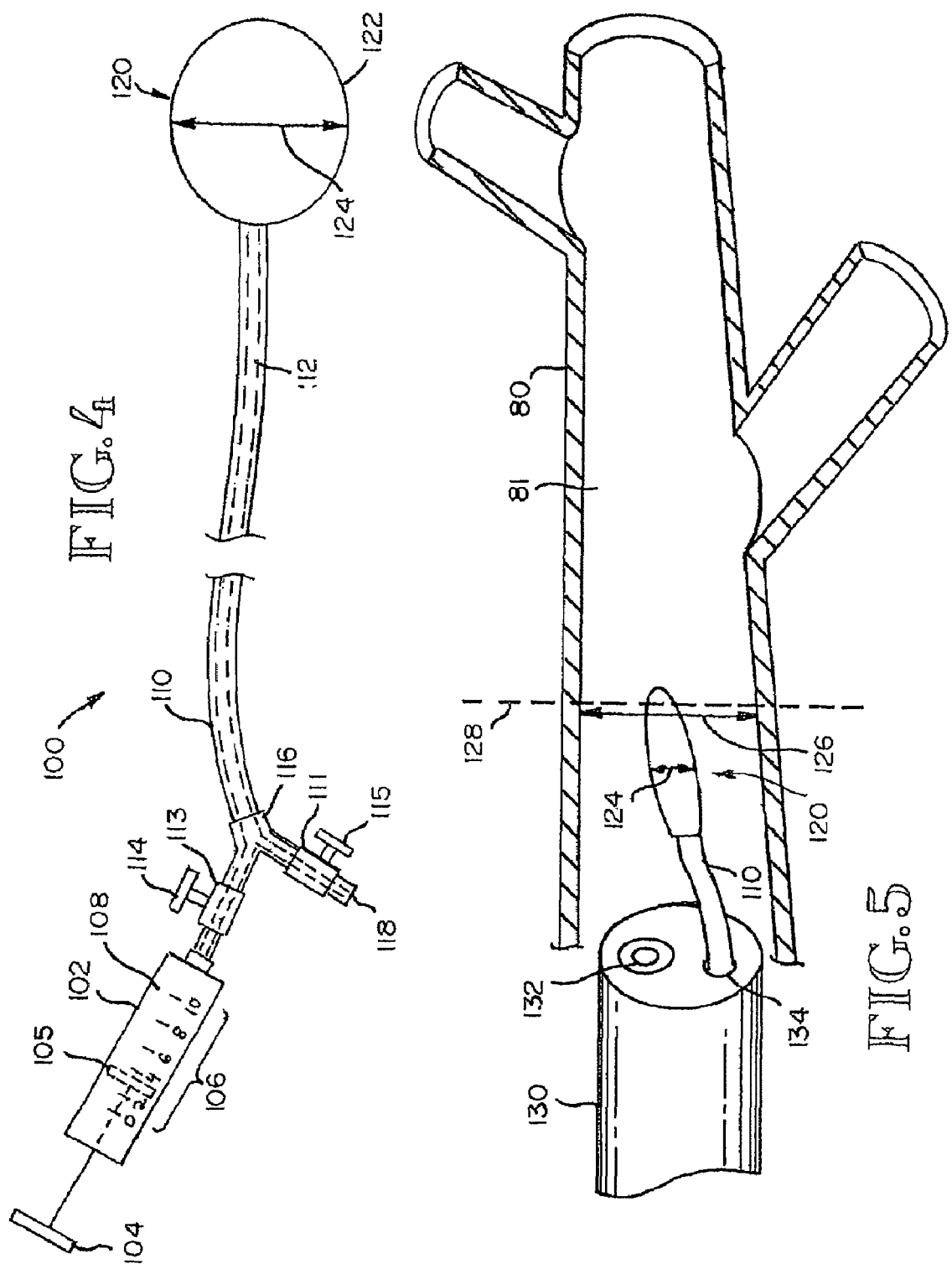

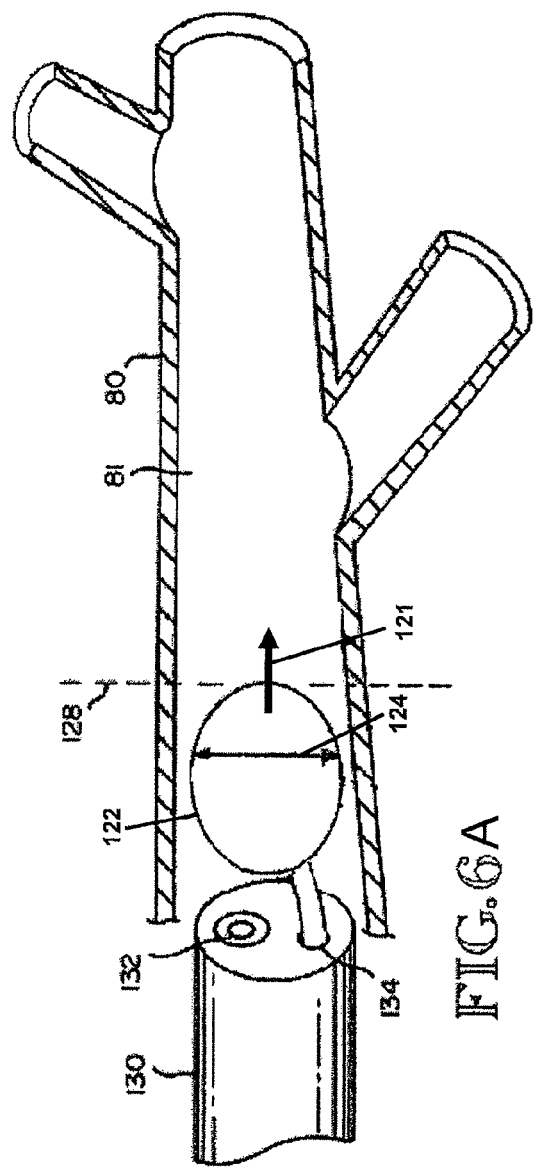
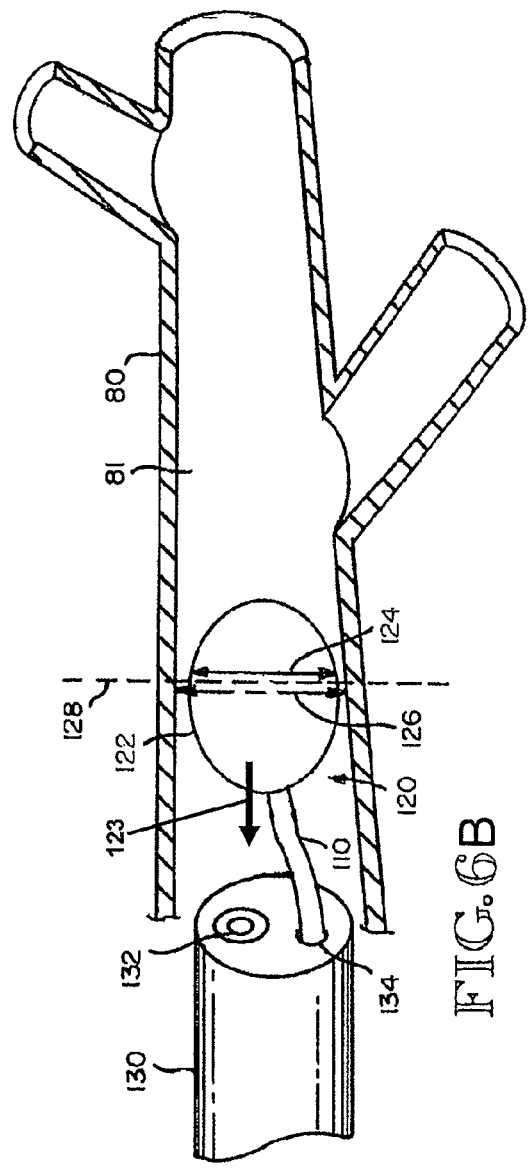

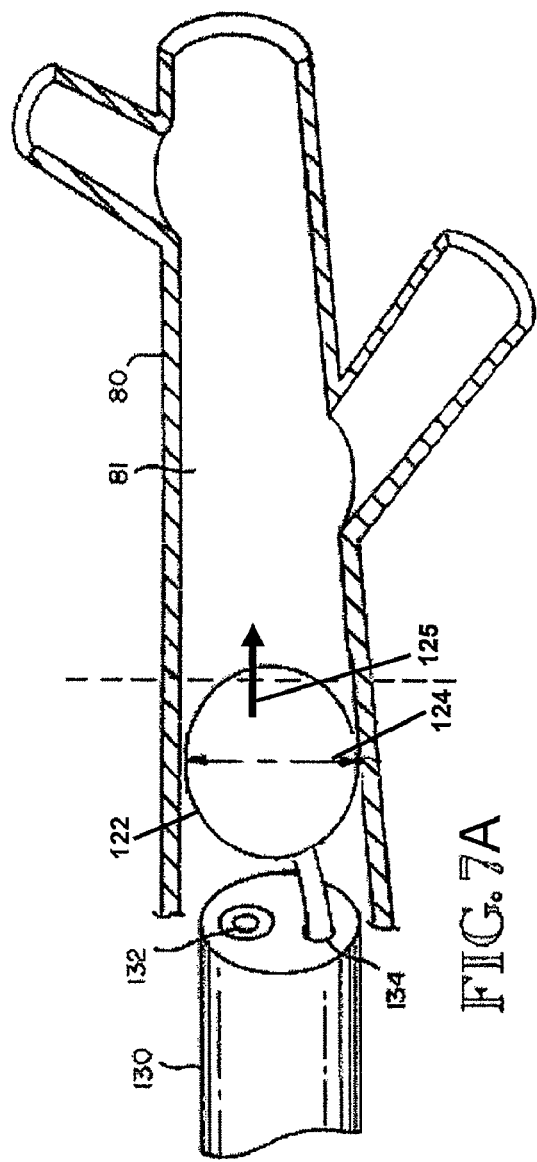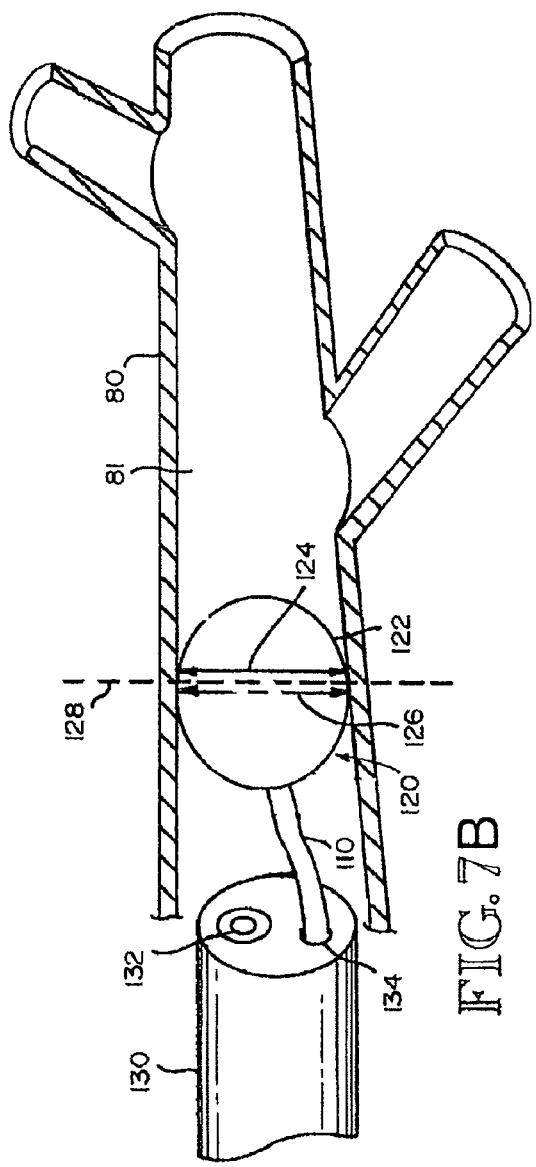
FIG. 7A
FIG. 7B

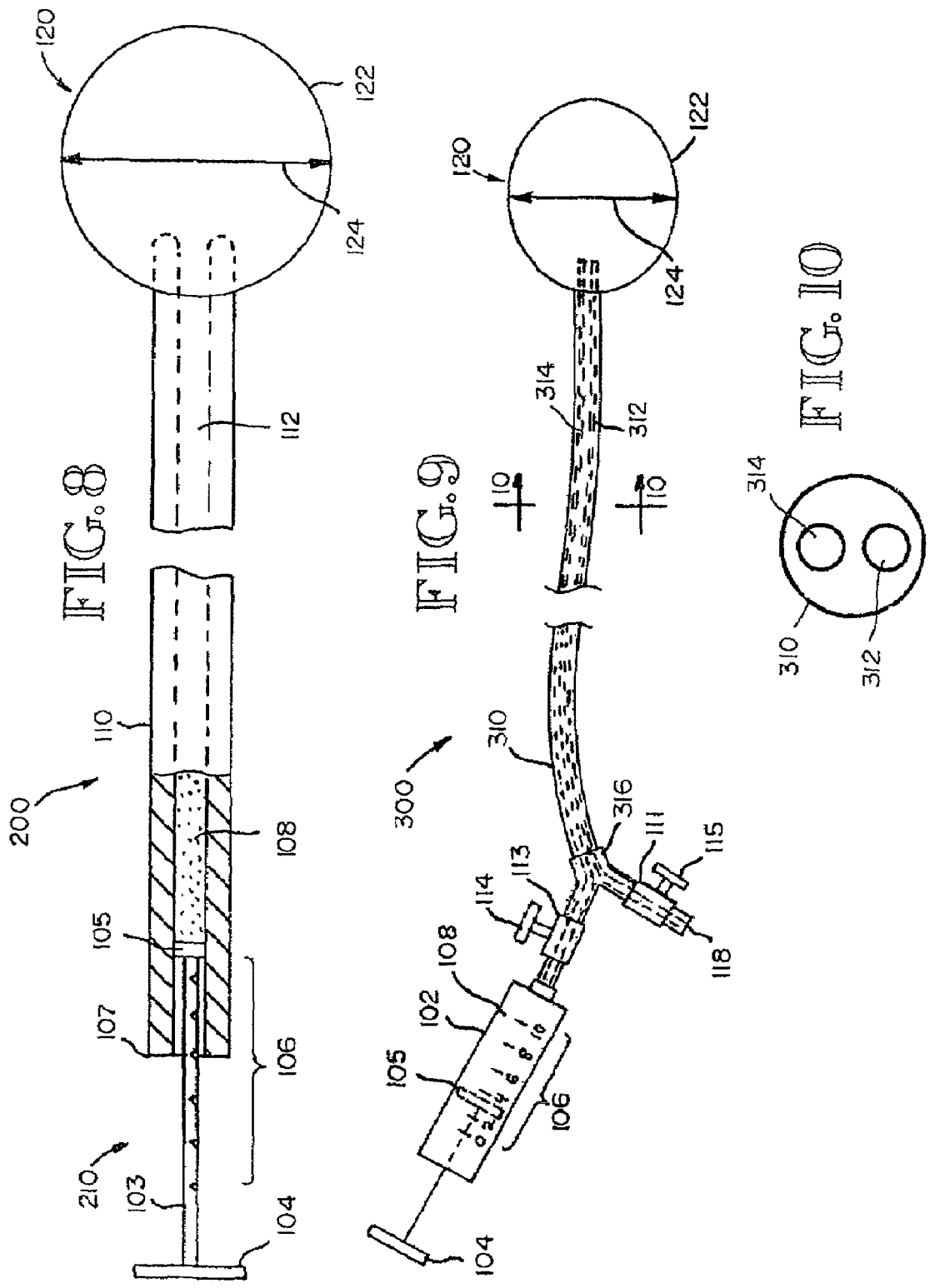

DEVICE AND METHOD FOR MEASURING THE DIAMETER OF AN AIR PASSAGEWAY

This application is a continuation of U.S. patent application Ser. No. 10/254,392, filed on Sep. 24, 2002 now abandoned. The entire contents of the above-noted prior patent application is hereby incorporated by reference herein and made a part of this specification.

BACKGROUND

The present invention is generally directed to a device and method for measuring the inside diameter of a body lumen and, more particularly, of air passageways. The present invention is more particularly directed toward measuring an inside diameter of an air passageway by transorally inserting a balloon having a known volume-to-diameter relationship in the air passageway, expanding the balloon with a volume of fluid to a known transverse diameter, and determining that the transverse diameter is adjacent to opposing portions of an interior wall of the air passageway.

Several emerging technologies employ devices placed in the air passageways to diagnose and treat conditions of the lung, conditions of organs and body structures that are in proximity to the lungs, and conditions that are systemic. For example, a treatment for Chronic Obstructive Pulmonary Disease (COPD) involves placing obstructing devices in selected air passageways to collapse lung portions distal of the obstructing devices. The devices are typically placed in air passageways between approximately 4 and 10 mm in diameter.

The performance of intra-bronchial devices may be enhanced by sizing the device to fit the air passageway. However, no method or device presently exists for determining the inside diameter of an air passageway. There is a need in the art for quickly and economically measuring the inside diameter of an air passageway to assist in selecting the size of an obstructing device.

In view of the foregoing, there is a need in the art for a new and improved apparatus and method for measuring the inside diameter of air passageways.

SUMMARY

The invention provides a device for measuring an inside diameter of a body lumen, such as an air passageway. The device includes a flexible catheter, and a member carried on a distal tip of the catheter, the member having a known transverse dimension and arranged for placement adjacent to opposing portions of an interior wall of the air passageway.

The invention further provides a device for measuring the diameter of an air passageway. The device includes a flexible catheter having an inflation lumen, a fluid dispenser in fluid communication with the inflation lumen and operable to communicate a measurable fluid volume change with the inflation lumen, and an expandable member in fluid communication with the inflation lumen and having a known relationship between fluid volume and a changeable transverse dimension, the transverse dimension being changeable in response to fluid volume changes of the fluid dispenser and arranged for placement adjacent to opposing portions of an interior wall of the air passageway. The expandable member may include a balloon of compliant material. The expandable member may be dimensioned for transoral placement into the air passageway. The expandable member may have a collapsed configuration for placement in the air passageway and an expanded configuration for measuring a diameter of the air passageway. The expandable member may be arranged to transition from an expanded configuration to a collapsed configuration while in the air passageway, and then to transition from the collapsed configuration to a re-expanded configuration for measuring the diameter of another air passageway. The catheter may include configuration to be steerable within bronchi. The catheter may include an expansion lumen and a purge lumen. The transverse dimension of the expandable member may be arranged to have a maximum transverse dimension of between 3 mm and 12 mm. The fluid dispenser may comprise a syringe or a syringe pump, and may further include gradations corresponding to air passageway diameters. The fluid dispenser may include a piston and a proximal portion of the inflation lumen cooperatively acting as a piston/cylinder combination arranged to communicate a measurable fluid volume change with another portion of the inflation lumen in communication with the expandable member. The fluid communicated to the expandable member may include a radiopaque contrast substance. The expandable member may include a radiopaque contrast marker arranged for visualization of the changeable transverse dimension by fluoroscopy. The catheter may have a distal end, and the expandable member may be carried on the catheter proximal to the distal end. The device may further include a visualization device for observing adjacency of the transverse dimension and opposing portions of the interior wall of the air passageway. The visualization device may include a bronchoscope or a fluoroscope.

The invention still further provides an assembly for measuring an inside diameter of an air passageway. The assembly includes a flexible catheter having an inflation lumen, the inflation lumen being arranged for fluid coupling with a fluid dispenser operable to communicate a measurable fluid volume change with the inflation lumen, and an expandable member in fluid communication with the inflation lumen and having a known relationship between fluid volume and a changeable transverse dimension, the transverse dimension of the expandable member being changeable in response to fluid volume changes of the fluid dispenser and arranged for placement adjacent to opposing portions of an interior wall of the air passageway. The expandable member may be carried on the catheter. The catheter may have a distal end, and the expandable member may be carried proximate to the distal end of the catheter. The expandable member may comprise a complaint material, and may be a balloon. The assembly may further include a visualization device for observing adjacency of the transverse dimension and opposing portions of the interior wall of the air passageway. The visualization device may include a bronchoscope or a fluoroscope.

The invention also provides a method of measuring an air passageway diameter. The method includes the steps of placing a balloon member in the air passageway having a known transverse dimension, and determining that the known transverse dimension is adjacent to opposing portions of an inner periphery of the air passageway.

In accordance with one embodiment, the method includes the steps of placing an expandable member in the air passageway, the expandable member changeable in a transverse dimension and having a known relationship between fluid volume and changeable transverse dimension, changing the changeable transverse dimension of the expandable member to a known transverse dimension by changing the fluid volume of the expandable member, and determining that the known expanded transverse dimension is adjacent to opposing portions of an inner periphery of the air passageway. The method may include the further step of placing a fluid dispenser operable to communicate a measurable fluid volume change into fluid communication with the expandable member, and the step of changing to a known transverse dimension includes the further step of measurably changing the volume of fluid in the expandable member with the fluid dispenser. The fluid dispenser may comprise a syringe. The fluid dispenser may include gradations related to air passageway diameter, and the step of determining air passageway diameter may include the further step of observing the gradations. The step of placing an expandable member in the air passageway may include the further step of transorally placing the expandable member in the air passageway. The step of determining may include the further step of visually observing adjacency, which may include using a visualization device or a fluoroscope. The expandable member may include a radiopaque contrast substance arranged to enhance viewing the changeable transverse dimension, and the step of determining adjacency may use fluoroscopy. The expandable member may include a balloon of compliant material.

The invention further provides a device for measuring an inside diameter of a body lumen is provided. The device includes means for placing an expandable member having a known transverse dimension in the air passageway, and means for determining that the known transverse dimension is adjacent to opposing portions of an inner periphery of the air passageway.

The invention still further provides a device for measuring an inside diameter of an air passageway. The device includes means for placing an expandable member in the air passageway, the expandable member changeable in a transverse dimension and having a known relationship between volume and changeable transverse dimension, means for changing the changeable transverse dimension to a known transverse dimension, and means for determining that the known transverse dimension is adjacent to opposing portions of an inner periphery of the air passageway.

These and various other features as well as advantages which characterize the present invention will be apparent from reading the following detailed description and a review of the associated drawings.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify like elements, and wherein:

FIG. 2 is a perspective view of the bronchi emphasizing the upper right lung lobe;

FIG. 4 illustrates an air passageway inside diameter measuring device in accordance with the present invention;

FIG. 5 illustrates an initial step in measuring an inside diameter of an air passageway at a measuring location with the measuring device of FIG. 4, in accordance with an aspect of the invention;

FIGS. 6A and 6B illustrate intermediate step of measuring an inside diameter of an air passageway at measuring location with the measuring device FIG. 4, in accordance with an aspect of the invention;

FIGS. 7A and 7B illustrate a final step in measuring an inside diameter of an air passageway at measuring location with the measuring device of FIG. 4, in accordance with an aspect of the invention; and FIG. 8 illustrates an air passageway inside diameter measuring device with a partial cross-section illustrating an integral fluid dispenser, in accordance with the present invention;

FIG. 9 illustrates an air passageway inside diameter measuring device with a catheter having a plurality of lumens, in accordance with the present invention. FIG. 10 is cross-sectional view of the catheter 310: and FIG. 10 is a cross-sectional view of the catheter of FIG. 9 illustrating the plurality of lumens.

DETAILED DESCRIPTION

Figure 1:
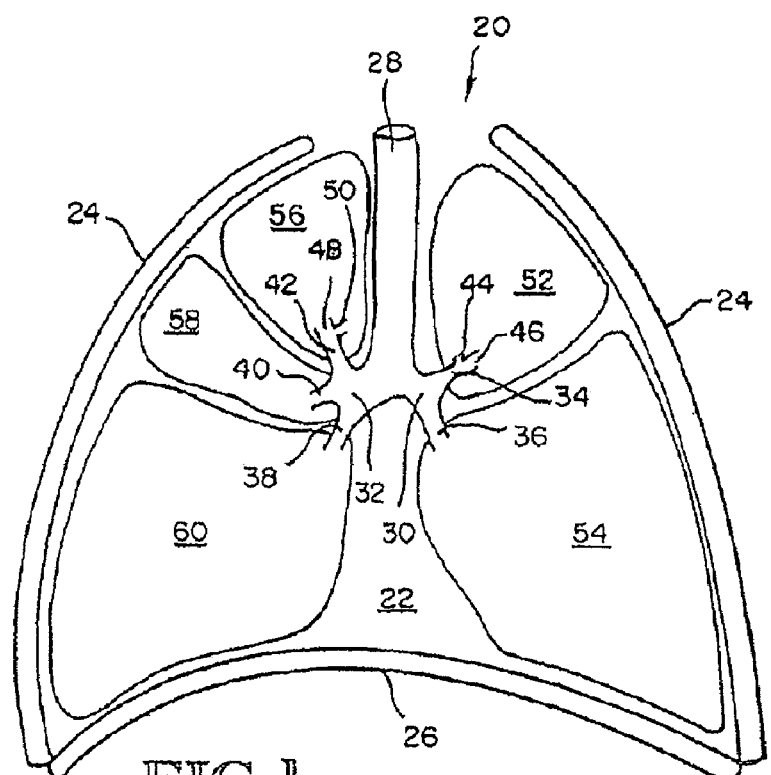
FIG. 1 is a sectional view of a healthy respiratory system.

In the following detailed description of exemplary embodiments of the invention, reference is made to the accompanying drawings, which form a part hereof. The detailed description and the drawings illustrate specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined only by the appended claims.

Throughout the specification and claims, the following terms take the meanings explicitly associated herein unless the context dictates otherwise. The meaning of "a", "an", and "the" include plural references. The meaning of "in" includes "in" and "on." Referring to the drawings, like numbers indicate like parts throughout the views. The term "coupled" means either a direct connection between the things that are coupled, or an indirect connection through one or more intermediary devices. Additionally, a reference to the singular includes a reference to the plural unless otherwise stated or inconsistent with the disclosure herein. Additionally, the term "fluid" means a substance that has no fixed shape and yields easily to external pressure, such as a gas and especially a liquid.

FIG. 1 is a sectional view of a healthy respiratory system. The respiratory system 20 resides within the thorax 22 that occupies a space defined by the chest wall 24 and the diaphragm 26.

The respiratory system 20 includes trachea 28; left mainstem bronchus 30 and right mainstem bronchus 32 (primary, or first generation); and lobar bronchial branches 34, 36, 38, 40, and 42 (second generation). FIG. 1 also illustrates segmental branches 44, 46, 48, and 50 (third generation). Additional sub-branches are illustrated in FIG. 2. The respiratory system 20 further includes left lung lobes 52 and 54 and right lung lobes 56, 58, and 60. Each bronchial branch and sub-branch communicates with a different portion of a lung lobe, either the entire lung lobe or a portion thereof. As used herein, the term "air passageway" is meant to denote either a bronchi or bronchioli, and typically means a bronchial branch of any generation.

A characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax, which in turn causes exhalation of the lung lobes.

FIG. 2 is a perspective view of the bronchi emphasizing the upper right lung lobe 56. In addition to the bronchial branches illustrated in FIG. 1, FIG. 2 illustrates subsegmental bronchial branches 80, 82, 84, 86, 88, and 89 (fourth generation) providing air circulation to superior right lung lobe 56. The fifth- and sixth-generation bronchial branches are illustrated, but not given reference numbers.

The air passageways branch out, much like the roots of a tree. The bronchial segments branch into six generations or orders, and the bronchioles branch into approximately another three to eight generations or orders. Typically, each generation has a smaller diameter than its predecessor. The inside diameter of a generation varies depending on the particular bronchial branch, and further varies between individuals. For example, a typical lobar bronchus 42 (third generation) providing air circulation to the upper right lobe 56 has an internal diameter of approximately 1 cm. A typical segmental bronchi 48 (fourth generation) has an internal diameter of approximately 4 to 7 mm. The fifth and sixth generations (no reference numbers) are each proportionately smaller. The bronchial segments include annular ligaments and irregularly located cartilages that provide structure and resilience. The cartilages become increasingly sparse as the bronchial segments become smaller in diameter. The bronchioles do not have ligaments and cartilages.

Figure 3:
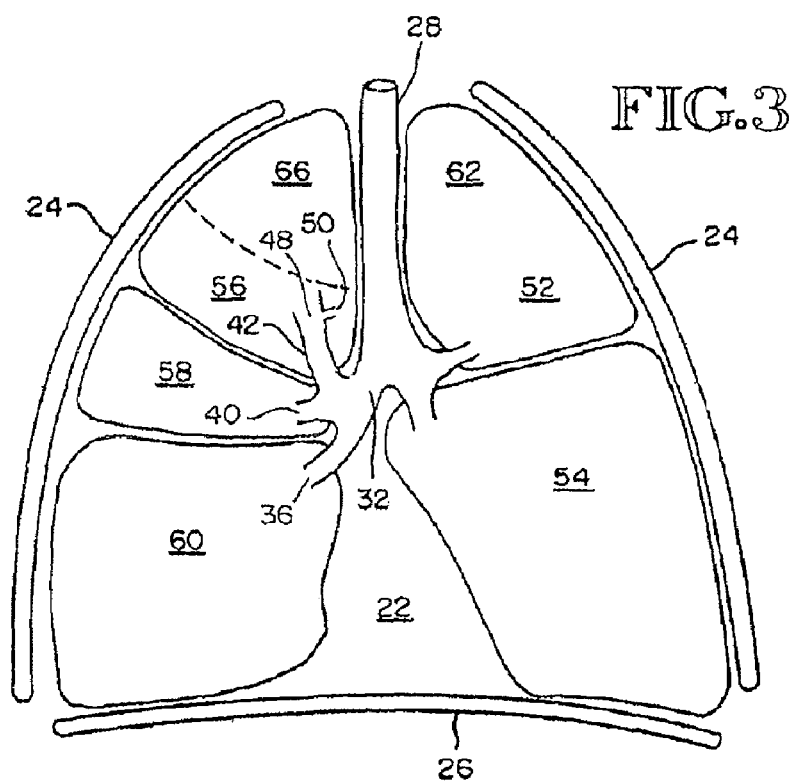
FIG. 3 illustrates a respiratory system suffering from COPD.

FIG. 3 illustrates a respiratory system suffering from COPD. In contrast to the lobes of FIG. 1, here it may be seen that the lung lobes 52, 54, 56, 58, and 60 are enlarged and that the diaphragm 26 is not arched but substantially straight. Hence, this individual is incapable of breathing normally by moving diaphragm 26. Instead, in order to create the negative pressure in thorax 22 required for breathing, this individual must move the chest wall outwardly to increase the volume of the thorax. This results in inefficient breathing causing these individuals to breathe rapidly with shallow breaths.

It has been found that the apex or segmental portions 62 and 66 of the upper lung lobes 52 and 56, respectively, are most affected by COPD. Hence, bronchial sub-branch obstructing devices are generally employed for treating the apex 66 of the right, upper lung lobe 56. The insertion of an obstructing member or a plurality of obstructing members treats COPD by deriving the benefits of lung volume reduction surgery without the need of performing the surgery. The intra-bronchial obstructions may be anchored in the air passageway to prevent movement or expulsion. In addition to treating COPD, it is presently contemplated that the intra-bronchial obstructions will be used for other purposes, including delivery of therapeutic substances.

The COPD treatment contemplates permanent collapse of a lung portion using at least one intra-bronchial obstruction. The collapse leaves extra volume within the thorax for the diaphragm to assume its arched state for acting upon the remaining healthier lung tissue. This should result in improved pulmonary function due to enhanced elastic recoil, correction of ventilation/perfusion mismatch, improved efficiency of respiratory musculature, and improved right ventricle filling. The treatment of COPD may include several intra-bronchial obstructing members being inserted in air passageways to form a redundant array. For example, if the volume of apex 66 of the right, upper lung lobe 56 were to be reduced, obstructing devices may be deployed in the four, fifth-generation air passageways branching off of the fourth-generation bronchial branches 80 and 82, redundant obstructing members placed in the fourth-generation bronchial branches 80 and 82, and another redundant obstructing member placed in the third-generation branch 50.

The physical characteristics of the obstructing devices currently available limit the range of air passageway diameters that a particular device can obstruct. The limiting characteristics include both the range of air passageway diameters that a single device can obstruct, and the range of air passageway diameters that can be engaged by anchors of the obstructing device. Use of anchors can allow the obstructing member to be relatively loosely fitted against the air passageway wall, which may preserve mucociliary transport of mucus and debris out of the collapsed lung portion. Thus, obstructing devices are provided in a variety of sizes for the various sizes of air passageways.

The present invention supports the use of intra-bronchial obstructing devices by enabling the inside diameter of the air passageway to be measured so that an appropriately sized obstructing device may be selected. As will be appreciated by those skilled the in art, the present invention may be used in conjunction with placing any type of obstructing member in an air passageway, including a plug, or a member that allows air passage in one direction but not another.

FIG. 4 illustrates an air passageway inside diameter measuring device 100, in accordance with the present invention. Measuring device 100 includes a fluid dispenser 102, a fluid 108, a flexible catheter 110, stopcocks 111 and 113, a junction fitting 116, and an expandable member 120.

The fluid dispenser (illustrated as a syringe 102) may be any device known in the art suitable for ejecting a measurable volume of the fluid 108 in amounts necessary to fill the expandable member 120. The fluid dispenser may be manually, mechanically, or electrically operated, or some combination thereof. The fluid dispenser may include a syringe, a syringe pump, or other piston/cylinder arrangement, or may be a deformable compartment or chamber. The fluid dispenser may be a separate device from the flexible catheter 110, or may be incorporated into it. The syringe 102 of FIG. 4 includes visually readable gradations 106 that correspond to air passageway diameters, and is illustrated with air passageway diameters ranging between zero and 10 mm. The gradations 106 may reflect any range of anticipated air passageway diameters. The syringe 102 also includes a handle 104 connected to a piston 105, and arranged such that moving the handle 104 transmits the motion to the piston 105, and the motion is further transmitted to the fluid 108.

The fluid 108 may be any fluid suitable for use within the human body, such as a saline solution. A gas may be used, but a liquid is preferred to provide ease of use and readability in the syringe 102. The fluid 108 may include a radiopaque contrast substance, such as diatrizoates and Iohexol.

The flexible catheter 110 may be any flexible, steerable, elongated tubular member arranged for transoral or transnasal insertion into an air passageway, and may be made from any suitable material known in the art, such as polyethylene. The catheter 110 includes an inflation lumen 112 arranged to be in fluid communication with the syringe 102. The catheter 110 is also arranged to carry and be in fluid communication with the expandable member 120. In an embodiment, catheter 110 has an external diameter of approximately 2 mm. The catheter 110 may include opaque markings visible under fluoroscopy, such as gold or stainless steel, or other markings visible under other visualization methods.

The stopcocks 111 and 113 can be opened and closed by operating handles 115 and 114 respectively. The stopcocks 111 and 113 may be made from any material suitable for extracorporeal use. Tubular member 118 is used to direct any fluid 108 drained from the device 100.

The expandable member (illustrated as expandable balloon 120) includes a changeable transverse dimension 126, an outer periphery 122 of the changeable transverse dimension 126, and an interior inflatable cavity (not shown). The inflatable balloon 120 is generally arranged for intra-bronchial use, and may be made of any thin, flexible complaint or elastic surgical material suitable for use in air passageways known in the art, such as polyurethane, silicone, and natural latex used for low pressure balloons. The compliant material provides a measurable or determinable relationship between balloon volume and the changeable transverse dimension 124. Balloon 120 may have any transverse cross-sectional shape that can be expanded adjacent to opposing portions of an air passageway wall. For example, while balloon 120 is generally described herein as having a round, expanded cross-section with a generally uniform single transverse dimension, the balloon 120 may be any shape having a transverse dimension that can be expanded to contact opposing portions of an interior wall of an air passageway. For example, the balloon 120 may be an ellipsoidal transverse cross-section having a changeable transverse dimension that is expandable adjacent to opposing portions of an interior wall of air passageway 81. For purposes of clarity, aspects of the invention are described herein using a balloon 120 that expands into a round cross-section having an expanded transverse dimension that is a diameter. However, as stated above, the invention is not so limited. The balloon 120 may be carried on the distal end of the catheter 110, or proximate to the distal end of the catheter 110.

In FIG. 4, the balloon 120 is illustrated in a partially expanded state. The balloon 120 and the catheter 110 are arranged for transoral placement into an air passageway using minimally invasive methods, such as a working lumen of a bronchoscope. The balloon 120 has a deflated configuration for insertion and passage through a working lumen, and for movement within air passageways. In its deflated state, the balloon 120 is approximately 10 mm in length and has a collapsed diameter suitable for passage through a working channel of a bronchoscope, which presently is approximately 2-3 mm. In its expanded state, the balloon 120 should be capable of expanding to more than the anticipated cross-sectional area of the air passageway being measured. Typically, the air passageway inside diameters being measured are not expected to exceed 10 mm in diameter, so the balloon 120 may have an maximum expanded diameter of approximately 12 mm. Because the air passageway diameter changes noticeably over a short distance, both the deflated and inflated lengths of the balloon are minimized so that a measurement for a particular location is not affected by the distal narrowing or proximal widening.

Junction fitting 116 has a single lumen that fluid couples the lumen 112 of catheter 110 to the lumens of stopcocks 111 and 113. The fluid 108 contained in syringe 102 is fluid coupled to the interior cavity of balloon 120 through the lumen of stopcock 113 and the lumen 112 of catheter 110. The fluid coupling creates fluid communication between the syringe 102 and the balloon 120 such that, when stopcock 113 is open, any change in the fluid volume of the syringe 102 is inversely translated into a change in the fluid volume of the balloon 120. The fluid 108 and any air contained in the interior cavity of balloon 120 or lumen 112 may be drained through the lumen of stopcock 111 and out tubular member 118 by moving handle 115 to an open position.

The air passageway diameter gradations 106 may be marked in millimeter gradations on the syringe 102 because the compliant material used for the balloon 120 provides a known relationship between the volume of the balloon 120 and its transverse dimension 124. The known relationship continues to at least when the balloon 120 is initially expanded adjacent to opposing portions of an interior wall of the air passageway. The gradations 106 may start at "0" or another convenient increment such as 2 mm, and are calibrated to correspond to the transverse dimension of the expanded balloon 120, and thus the air passageway. As the handle 104 is pushed from the starting gradation, a measurable volume of the fluid 108, reflected by the other gradations of the gradations 106, is ejected from the syringe 102 and forced into the balloon 120 through fluid communication by the lumen 112 of catheter 110. Because the relationship between the volume and the changeable transverse dimension of the balloon 120 is known, the transverse dimension 124 of the expanded balloon 120 is known from the volume of the fluid 108 ejected from the syringe 102. The transverse dimension 124 is known or determined by observing the location of the syringe piston 105 with respect to the gradations 106. The gradations 106 may be marked in volume gradations, such as milliliters, and a conversion table used to convert volume to transverse dimension 124.

Correlation between volume and transverse dimension 124 for a particular balloon configuration may be established using a test bench. Balloon 120 is expanded in a series of openings with several known diameters, and a correlation is established between the expanded volumes of the test balloon 120 and the several known diameters. The syringe gradations 106 are established correlating the volume of the fluid 108 displaced by movement from the "0" gradation with the known diameter. Each individual measuring device 100 may have its gradations determined on a test bench. Alternatively, the physical parameters of the syringe 102 and the balloon 120 may be standardized, allowing standardized gradation markings 106.

FIG. 5 illustrates an initial step in measuring an inside diameter 126 of an air passageway 81 at a measuring location 128 with the measuring device 100 of FIG. 4, in accordance with an aspect of the invention. In an embodiment, the measuring device 100 is provided with its elements fluid coupled together and filled with fluid 108. The syringe 102, the lumen 112, and the collapsed balloon 120 are filled with saline solution as fluid 108, and any air bubbles in the fluid 108 have been removed. Further, the device 100 may be generally provided with the balloon 120 deflated to a minimum transverse dimension 124 of about 2 mm for insertion and movement, all air bubbles eliminated from the fluid 108, and the syringe piston 105 aligned with a gradation 106 representing the transverse dimension 124. For clarity, inside diameter 126 is illustrated slightly displaced from measuring location 128. However, it is contemplated that measuring device 100 will measure the inside diameter 126 at the measuring location 128.

An initial step includes transorally placing the distal end of catheter 110 and the balloon 120 into the trachea 28 and steering them into the air passageway 81 of the bronchus 80 to the measuring location 128. This may be accomplished by any method and/or device known in the art. The catheter 110 may be steered into air passageway 81 by being carried in a working lumen 134 of a bronchoscope 130; associated with and then steered by the bronchoscope 130; inserted after the bronchoscope 130 is proximate to the measuring location 128 and steered adjacent to the shaft of the bronchoscope 130; or steered using imaging/visualization techniques, such as computed tomography or radiography.

Continuing with FIG. 5, an embodiment is illustrated where a distal tip of the bronchoscope 134 has been steered into air passageway 81 for dimensioning. Once the distal tip is in proximity to measuring location 128, another step includes deploying the balloon 120 and the distal end of the catheter 110 from the working lumen 134. The deployment may be observed with viewing element 132 of the bronchoscope 130. A further initial step includes advancing the balloon 120 until its transverse dimension 124 is about a balloon length proximal of the measuring location 128.

FIGS. 6A and 6B illustrate another step in measuring an inside diameter 126 of an air passageway 81 at measuring location 128 with measuring device 100 of FIG. 4, in accordance with an aspect of the invention. An intermediate step includes expanding the balloon 120 in the air passageway 81 to a first trial transverse dimension of the transverse dimension 124. The expansion is by opening stopcock 113 and advancing the handle 105 of the syringe 102 to eject a known volume of the fluid 108 into the inflation lumen 112 and correspondingly into the balloon 120. The ejected volume and resulting first trial transverse dimension are known by the gradations 106. The endoscopist may select the first trial transverse dimension to be slightly less than an estimated air passageway inside diameter 126. The endoscopist may estimate an air passageway inside diameter 126 based on the particular bronchial branch diameter to be measured. For example, if the targeted bronchial branch usually has air passageway inside diameter 126 between five and six millimeters, a first trial transverse dimension of four millimeters may be selected. In such a case, the stopcock handle 114 is moved to an open position, and the handle 104 pressed until the plunger 105 aligns with the 4 mm gradient of gradations 106. The stopcock handle 114 is then moved to a closed position, preventing the compliant characteristic of balloon 120 or contact with the air passageway 81 from forcing fluid 108 back into the syringe 102.

Another step includes advancing 121 the balloon 120 distally within the air passageway 81 until the transverse dimension 124 is proximate to the measuring location 128. The viewing element 132 is used to visually examine the periphery 122 of the balloon 120 at transverse dimension 124 to determine whether first trial transverse dimension is adjacent to the inside wall of the air passageway 81. As used herein, "adjacent" or "adjacency" means closing the space between the periphery 122 of the balloon 120 at transverse dimension 124 and an interior periphery of an interior wall of the air passageway 81. FIG. 6A illustrates a situation where the first trial transverse dimension of 4 mm does not result in the transverse dimension 124 being adjacent to opposing portions of an inner periphery of the air passageway wall 81. Failure of first trial transverse dimension 124 to achieve adjacency is observed through the viewing element 132. The endoscopist may select a second trial transverse dimension, which may be 5 mm based on the separation observed between the periphery 122 and the inner periphery of the air passageway wall 81.

FIGS. 7A and 7B illustrate a final step in measuring an inside diameter 126 of an air passageway 81 at measuring location 128 with measuring device 100 of FIG. 4, in accordance with an aspect of the invention. The balloon 120 is retracted 123 from measuring location 128 by about a balloon 120 length to allow room to change to the second trial transverse dimension, which is 5 mm in the example being illustrated herein. To change the transverse dimension 124 to the second trial transverse dimension, the endoscopist changes the volume of fluid 108 in the balloon 120 in substantially the same manner as the first trial transverse dimension was established. If the first trial transverse dimension had been larger than the inside diameter 126, the handle 104 would be retracted until the piston 105 aligns with a different second trial transverse dimension.

Another step includes re-advancing 125 the balloon 120 distally within the air passageway 81 as before until the transverse dimension 124 is located at the measuring location 128. The viewing element 132 is used to visually examine the periphery 122 of the balloon 120 at transverse dimension 124 to determine whether second trial transverse dimension 124 is adjacent to the inside wall of the air passageway 81. FIG. 7B illustrates the transverse dimension 124 adjacent to opposing portions of an inner periphery of the air passageway 81. If adjacency is not achieved, the endoscopist selects additional trial transverse dimensions and continues as described above until adjacency is achieved.

When the periphery 122 of transverse dimension 124 is adjacent to an interior periphery 81 of the air passageway 80, the expanded transverse dimension 124 of the balloon 120 is the same as the inside diameter 126 of the air passageway 81. In the embodiment illustrated in FIG. 7, adjacency between the periphery 122 of the balloon 120 and the inside wall of the air passageway 81 at measuring location 128 is visually confirmed by observation through the viewing element 132 of the bronchoscope 130. When adjacency exists, the diameter 126 at measuring location 128 is read by the alignment of the syringe piston 105 with one or more of the gradations 106, which would be 5 mm in the example. When the balloon 120 has an expandable transverse cross-section that is not round, the changeable transverse dimension 124 is expanded to a point where a portion of its periphery 122 at the measuring location 128 is adjacent to opposing portions of the interior periphery 81 of the interior wall of the air passageway 80.

After the measurement is taken, the measuring device 100 is arranged to allow the balloon 120 to be deflated by opening stopcock 113 and drawing the fluid 108 back into the syringe 102 while the balloon 120 is within the air passageway 81. The catheter 110 and the deflated balloon 120 may then be steered to another measuring location to measure another air passageway diameter 126.

FIG. 8 illustrates an air passageway inside diameter measuring device 200 with a partial cross-section illustrating an integral fluid dispenser 210, in accordance with the present invention. Measuring device 200 is structurally, functionally, and operationally similar to measuring device 100 of FIG. 4, except that it includes an integral fluid dispenser 210 instead of an external fluid dispenser.

Integral fluid dispenser 210 includes shaft 103, handle 104, piston 105, visually readable gradations 106, a portion of the proximal portion of lumen 112, and an index mark or point 107. The structure for changing the fluid volume of the integral fluid dispenser 210 is formed by the piston 105 and a proximal portion lumen 112 cooperatively acting as a piston/cylinder combination for communicating a measurable volume of fluid 108 into the interior inflatable cavity of balloon 120. Shaft 103 rigidly couples handle 104 to piston 105. Gradations 106 are incorporated into shaft 103, and read by alignment with index point 107 on the proximal end of catheter 110 in substantially the same manner as the gradations 106 of device 100 are read by alignment with the piston 105.

In operation, measuring device 200 and fluid dispenser 210 are arranged and function substantially similarly to measuring device 100 and its syringe as described in conjunction with FIGS. 4-7. When the handle 104 is advanced, the piston 105 communicates a measurable fluid volume change with the balloon 120, which is represented by gradations 106.

FIGS. 9 and 10 illustrate an air passageway inside diameter measuring device 300 with a catheter 310 having a plurality of lumens 312 and 314, in accordance with the present invention. FIG. 10 is a cross-sectional view of the catheter 310. Measuring device 300 is substantially similar in materials, arrangement, and operation to measuring device 100. Catheter 310 of measuring device 300 includes two lumens, inflation lumen 312 and purge lumen 314. Junction fitting 316 has two lumens that individually are in fluid communication with lumens 312 and 314, one lumen arranged to fluid couple the purge lumen 314 to the stopcock 111, and the other lumen arranged to fluid couple the inflation lumen 312 to the stopcock 113.

In operation, the purge lumen 314 promotes flow of entrapped air out of the syringe 102, catheter 310, and the balloon 120. A source of fluid 108 for purging, which may be a syringe similar to the syringe 102, is fluid coupled to junction fitting 316 and lumen 312. Stopcocks 111 and 113 are opened by appropriately moving handles 115 and 114 respectively, and fluid 108 is ejected from the syringe and flowed through collapsed balloon 120 to purge air from measuring device 300. Air and fluid 108 are drained from the measuring device 300 from the lumen of stopcock 111 at tubular member 118. The presence of the lumen 312 for communicating fluid 108 into the balloon 120 and the lumen 314 for purging air and fluid 108 from the balloon 120 facilitate purging entrapped air from the device 300. Once all air is purged, stopcocks 111 and 113 are closed. The purging source of fluid 108 is removed from junction fitting 316, and syringe 102 is then coupled. Measuring device 300 can then be used to measure the inside diameter of a body lumen as described in conjunction with measuring device 100. The above description includes embodiments of the invention providing a device and method for measuring an inside diameter of a body lumen, such as an air passageway in conjunction with placing an obstructing or valving device in the air passageway to reduce lung volume. However, the invention is not so limited. Other embodiments of the invention may be used to measure the inside diameter of an air passageway for placing other types of devices having other treatment objectives. Further, other embodiments of the invention may be used to measure a diameter of any body lumen for any procedure, including preparation for implanting a device or other medical procedure.

Although the present invention has been described in detail with reference to certain preferred embodiments, other embodiments are possible. Therefore, the spirit or scope of the appended claims should not be limited to the description of the embodiments contained herein. It is intended that the invention resides in the claims hereinafter appended.

What is claimed is:

1. A method of measuring an inside diameter of a native body lumen in a lung, the method comprising
   preparing a measuring device that comprises a non-cylindrical expandable member;
   inserting the member into the body lumen; and
   after positioning the member in the body lumen, expanding the member and, while the member is expanded, moving the member axially along the body lumen to a desired location in order to measure the size of the body lumen at the desired location;
   and then retracting the member, changing a diameter of the member and then advancing the member toward the desired location again.

2. The method of claim 1, wherein the member is positioned within a naturally substantially tapered portion of the body lumen when the member is expanded into the expanded configuration.

3. The method of claim 1, wherein the member is substantially ellipsoidal in shape when the member is in the expanded configuration.

4. The method of claim 1, wherein the expandable member is substantially spheroidal in shape when the member is in the expanded configuration.

5. The method of claim 1, wherein positioning the member in the body lumen comprises transorally placing the member in the body lumen.

6. The method of claim 1, wherein inserting the member into the body lumen comprises transorally placing the catheter and the balloon into the trachea and steering the catheter and the balloon toward the desired location.

7. The method of claim 1, wherein preparing the measuring device comprises fluidly coupling the member to a fluid source.

8. The method of claim 1, wherein preparing the measuring device comprises removing air bubbles from the measuring device.

9. The method of claim 1, wherein the fluid source comprises a plunger and a scale and the scale corresponds to various measurable diameters.

10. The method of claim 7, wherein the fluid source comprises a graduated syringe with graduations correlating to measurable diameters.

11. The method of claim 1 further comprising visually inspecting a periphery of the member to determine if the member is in contact with the body lumen.

12. A method of measuring an inside diameter of a native body lumen in a lung, the method comprising:
    preparing a measuring device for insertion into a patient by supplying fluid to a fluid source, a lumen of the measuring device and a collapsed balloon and by removing air bubbles from the fluid;
    positioning a distal end of the measuring device into a trachea of the patient and steering the distal end of the measuring device to a desired location in the native body lumen for measurement;
    expanding the balloon in the native body lumen to a first trial transverse dimension of a known first dimension and advancing the expanded balloon toward the desired location;
    examining a periphery of the balloon to determine whether the first dimension is adjacent to the inside wall of the native body lumen at the desired location; and
    retracting the balloon from the desired location and expanding or contracting the balloon in the native body lumen to a second trial transverse dimension of a known second dimension and readvancing the expanded balloon toward the desired location.

13. The method of claim 12, wherein preparing the measuring device comprises aligning a piston of the fluid source with a marking to indicate position.

14. The method of claim 12, wherein the distal end of the measuring device is steered by being positioned within a working channel of a bronchoscope.

15. The method of claim 12, wherein the distal end of the measuring device is steered by being associated with and then steered by a bronchoscope.

16. The method of claim 12, wherein the distal end of the measuring device is steered by moving along a shaft of an already-inserted bronchoscope.

17. The method of claim 12, wherein the distal end of the measuring device is steered using imaging or visualization techniques.

18. The method of claim 12, wherein the balloon of the measuring device is deployed once the distal end of the measuring device is proximate the desired location.

19. The method of claim 18, wherein the balloon is advanced until a transverse dimension of the balloon is about a balloon length from the desired location.

20. The method of claim 12, wherein expanding the balloon comprises opening a valve, inserting fluid into the balloon and closing the valve such that fluid cannot be forced out of the balloon once the balloon has been expanded.

21. The method of claim 12 further comprising reexamining the periphery of the balloon to determine whether the second dimension is adjacent to the inside wall of the native body lumen at the desired location.

22. The method of claim 12 further comprising collapsing the balloon and repositioning the distal end of the measurement device.

23. The method of claim 12 further comprising collapsing the balloon and removing the distal end of the measurement device from the patient.

24. A method of measuring an inside diameter of a native body lumen in a lung, the method comprising:
   preparing a measuring device for insertion into a patient by supplying fluid to a fluid source, a lumen of the measuring device and a collapsed balloon and by removing air bubbles from the fluid;
   positioning a distal end of the measuring device into a trachea of the patient and steering the distal end of the measuring device to a desired location in the native body lumen for measurement;
   expanding the balloon in the native body lumen to a first trial transverse dimension of a known first dimension and advancing the expanded balloon toward the desired location; and
   examining a periphery of the balloon to determine whether the first dimension is adjacent to the inside wall of the native body lumen at the desired location;
   wherein the balloon of the measuring device is deployed once the distal end of the measuring device is proximate the desired location, and wherein the balloon is advanced until a transverse dimension of the balloon is about a balloon length from the desired location.

25. The method of claim 24, wherein preparing the measuring device comprises aligning a piston of the fluid source with a marking to indicate position.

26. The method of claim 24, wherein the distal end of the measuring device is steered by being positioned within a working channel of a bronchoscope.

27. The method of claim 24, wherein the distal end of the measuring device is steered by being associated with and then steered by a bronchoscope.

28. The method of claim 24, wherein the distal end of the measuring device is steered by moving along a shaft of an already-inserted bronchoscope.

29. The method of claim 24, wherein the distal end of the measuring device is steered using imaging or visualization techniques.

30. The method of claim 24, wherein expanding the balloon comprises opening a valve, inserting fluid into the balloon and closing the valve such that fluid cannot be forced out of the balloon once the balloon has been expanded.

31. The method of claim 30 further comprising reexamining the periphery of the balloon to determine whether the second dimension is adjacent to the inside wall of the native body lumen at the desired location.

32. The method of claim 24 further comprising collapsing the balloon and repositioning the distal end of the measurement device.

33. The method of claim 24 further comprising collapsing the balloon and removing the distal end of the measurement device from the patient.

* * * * *

UNITED STATES PATENT AND TRADEMARK OFFICE
CERTIFICATE OF CORRECTION

PATENT NO. : 7,476,203 B2  
APPLICATION NO. : 11/260012  
DATED : January 13, 2009  
INVENTOR(S) : Devore et al.

Page 1 of 1

It is certified that error appears in the above-identified patent and that said Letters Patent is hereby corrected as shown below:

On the Title Page, Item (56) (Other Publications), Line 22, please Delete "Pyelo-broncial" and insert -- Pyelo-bronchial --, therefor.

On the Title Page, Item (56) (Other Publications), Line 25, please Delete "Intrattracheal" and insert -- Intratracheal --, therefor.

Col. 3, line 64, please Delete "illustrate" and insert -- illustrate an --, therefor.

Col. 3, line 64, please Delete "of" and insert -- in --, therefor.

Col. 3, line 66, please Delete "device" and insert -- of --, therefor.

Col. 12, line 17 (Approx) (In Claim 8), please Delete "claim 1," and insert -- claim 7, --, therefor.

Col. 12, line 20 (Approx) (In Claim 9), please Delete "claim 1," and insert -- claim 7, --, therefor.

Signed and Sealed this

Ninth Day of June, 2009

JOHN DOLL  
*Acting Director of the United States Patent and Trademark Office*